United States Patent
Cai et al.

(10) Patent No.: US 7,648,624 B2
(45) Date of Patent: *Jan. 19, 2010

(54) OXYGEN SENSOR

(75) Inventors: Xiaohua Cai, Needham, MA (US);
Kara Alesi, Winchester, MA (US);
Chung Chang Young, Weston, MA (US)

(73) Assignee: Nova Biomedical Corporation, Waltham, MA (US)

( * ) Notice: Subject to any disclaimer, the term of this patent is extended or adjusted under 35 U.S.C. 154(b) by 738 days.

This patent is subject to a terminal disclaimer.

(21) Appl. No.: 11/161,180

(22) Filed: Jul. 26, 2005

(65) Prior Publication Data

US 2007/0023296 A1    Feb. 1, 2007

(51) Int. Cl.
*G01N 27/26* (2006.01)
*G01F 1/64* (2006.01)

(52) U.S. Cl. .............. 205/782; 205/775; 205/777.5; 205/792; 204/403.14

(58) Field of Classification Search .............. 205/782, 205/792, 775, 775.5; 204/403.14
See application file for complete search history.

(56) References Cited

U.S. PATENT DOCUMENTS

| | | |
|---|---|---|
| 4,311,151 A | 1/1982 | Hagihara |
| 4,466,879 A | 8/1984 | Ho et al. |
| 4,476,870 A | 10/1984 | Peterson et al. |
| 4,672,971 A | 6/1987 | Otten |
| 4,930,506 A | 6/1990 | Ullrich |
| 5,007,424 A | 4/1991 | Ahsbahs et al. |
| 5,030,333 A | 7/1991 | Clark, Jr. |
| 5,089,421 A | 2/1992 | Dieffenbach |
| 6,190,612 B1 | 2/2001 | Berger et al. |

FOREIGN PATENT DOCUMENTS

WO    WO 03012422 A1 * 2/2003

OTHER PUBLICATIONS

Polgar et al., "Measurement of oxygen tension in unstirred blood with a platinum electrode," J. Appl. Physiol., 1960, 706-11, 15.
Mayers et al., "A rapid method for measuring blood oxygen content utilizing the oxygen electrode," J. Appl. Physiol., 1966, 1393-96, 21.
Fenner, "Oxygen monitoring in neonatal medicine," Biotelemetry, 1974, 227-38, 1.
Crockard et al., "Measurements of oxygen tension in the cerebral coretex of baboons," J. Neurol. Sci., 1976, 17-28, 27.

(Continued)

*Primary Examiner*—Nam X Nguyen
*Assistant Examiner*—Jennifer Dieterle
(74) *Attorney, Agent, or Firm*—Robert R. Deleault, Esq.; Mesmer & Deleault, PLLC

(57) ABSTRACT

An oxygen sensor has a laminated body with a fluid sample inlet end and an electrical contact end, a fluid sample inlet, a substantially flat test chamber communicating with the fluid sample inlet where the test chamber is adapted to collect a fluid sample through the sample fluid inlet, a working electrode and a reference electrode within the test chamber, and a reagent matrix disposed on the working electrode where the reagent matrix contains an oxidase, a reduced form of a redox mediator and a peroxidase.

18 Claims, 7 Drawing Sheets

OTHER PUBLICATIONS

Rithalia et al., "The performance characteristics of an intra-arterial oxygen electrode," Intensive Care Med., 1981, 305-7, 7.

Hagihara et al., "Intravascular oxygen monitoring with a polarographic oxygen cathode," J. Biomed. Eng., 1981, 9-16, 3.

Nilsson et al., "Polarographic PO2 sensors with heparinized membranes for in vitro and continuous in vivo registration," Scand. J. Clin. Lab. Invest., 1981, 557-63, 41. Claremont et al., "Continuous monitoring of blood PO2 in extracorporeal systems. An in vitro evaluation of a re-usable oxygen electrode," Anaesthesia, 1984, 362-9, 39.

Severinghaus et al., "History of blood gas analysis. IV. Leland Clark's oxygen electrode," J. Clin. Monit., 1986, 125-39, 2.

Nagaoka et al., "Antithrombogenic PO2 sensor for continuous intravascular oxygen monitoring," Biomaterials, 1990, 414-8, 11.

Suzuki et al., "Fabrication of a sensing module using micromachined biosensors," Biosens. Bioelectron, 2001, 725-33, 16.

Golde et al., "The oxygen optode: an improved method of assessing flap blood flow and viability," J. Otolaryngol., 1994, 138-44, 23.

\* cited by examiner

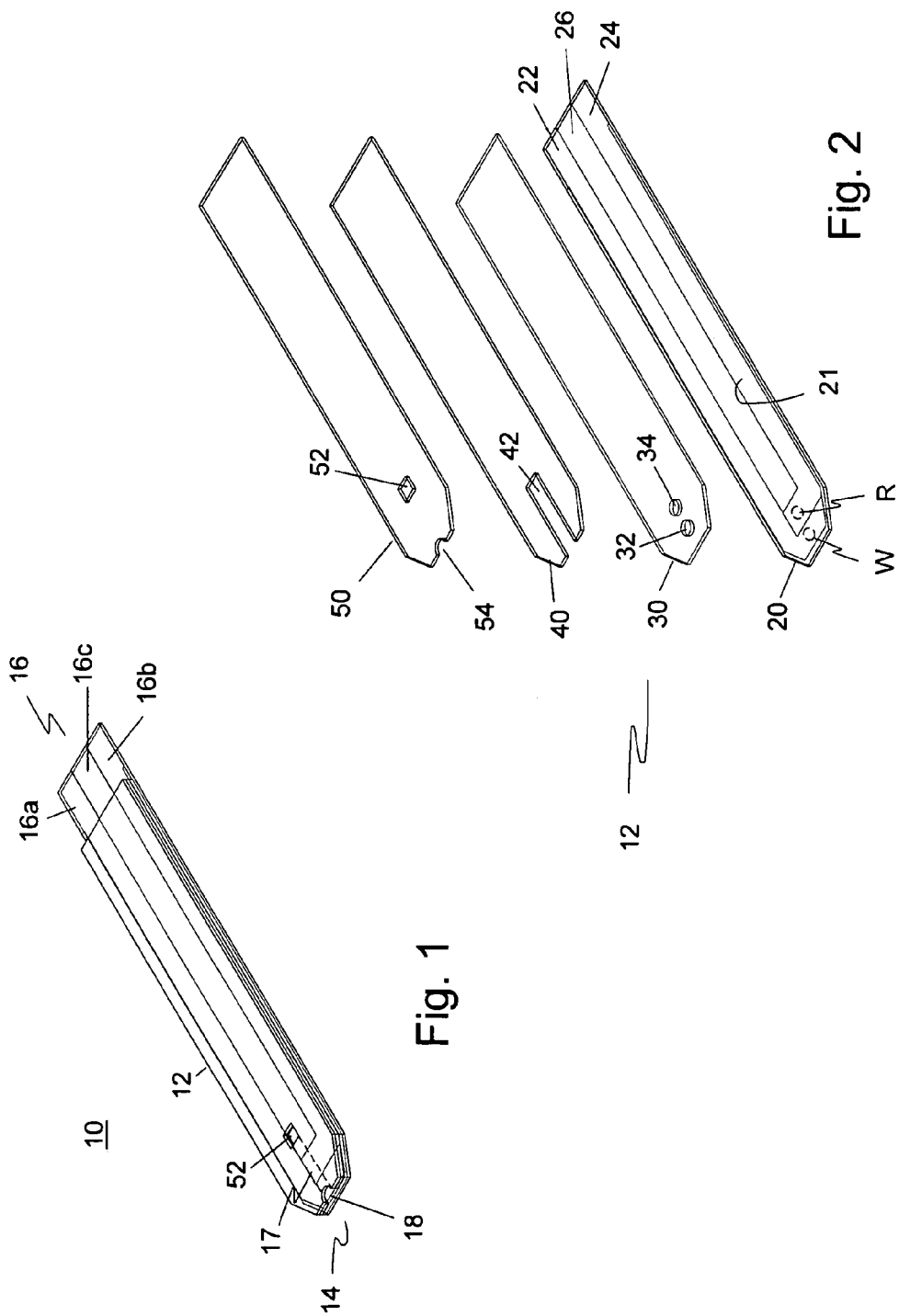

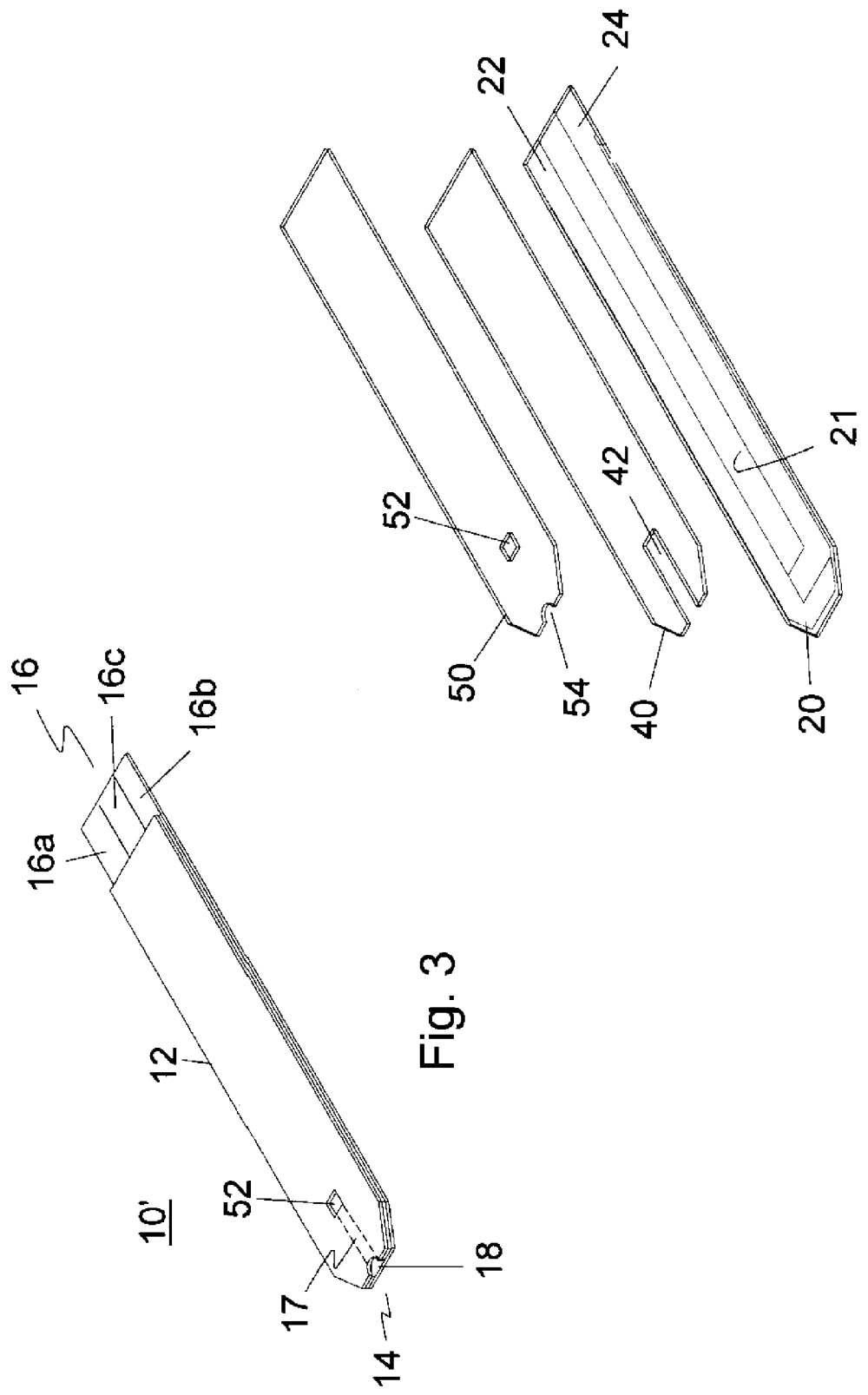

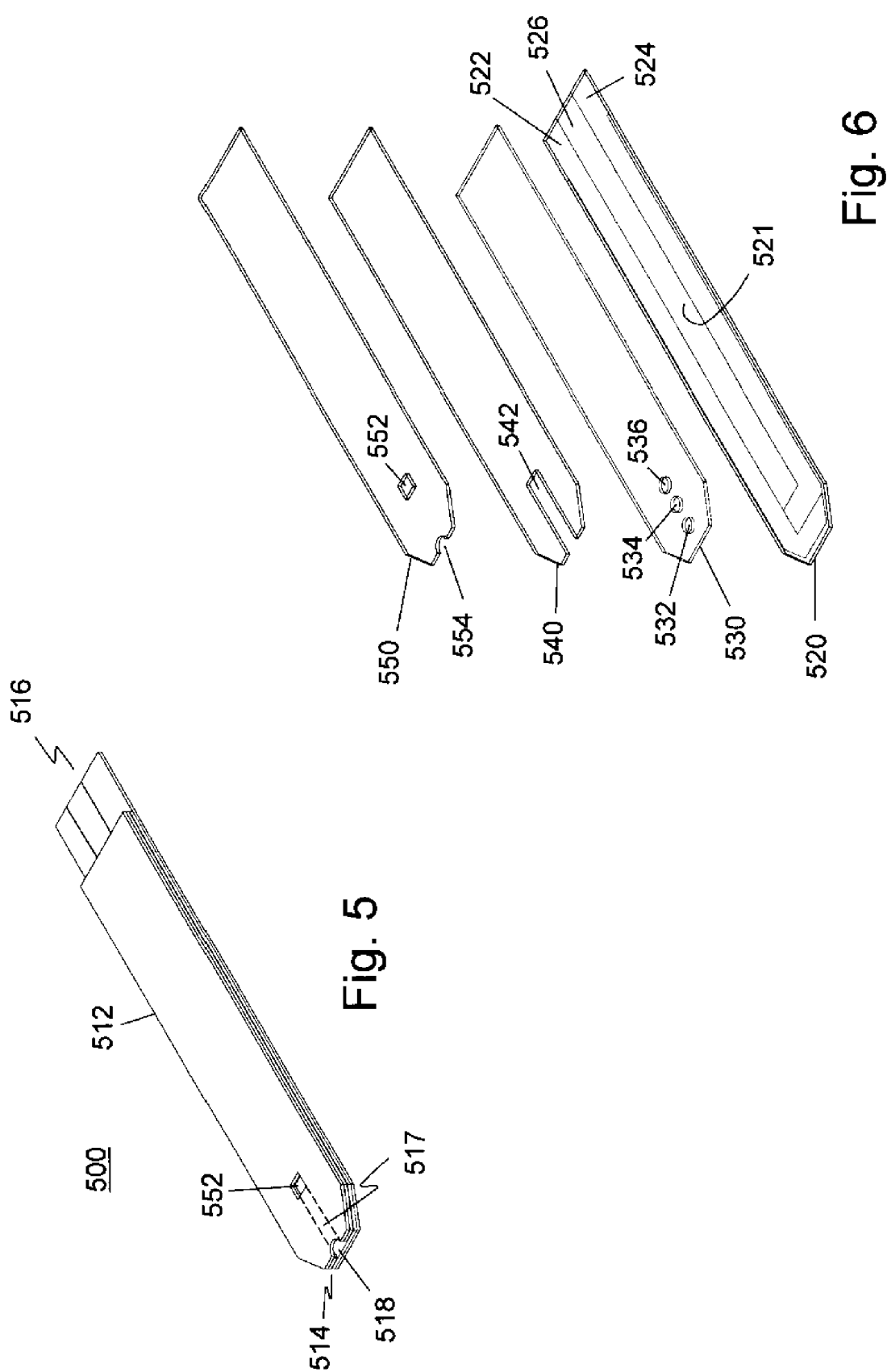

OXYGEN SENSOR

BACKGROUND OF INVENTION

1. Field of the Invention

The present invention relates generally to an electrochemical sensor used for the quantification of a specific component or analyte in a liquid sample. Particularly, the present invention relates to an electrochemical sensor for the detection of analytes present in biological fluids. More particularly, the present invention relates to a disposable electrochemical sensor for the in vitro detection of oxygen concentration.

2. Description of the Prior Art

Oxygen is an essential factor to aquatic life and human beings. The quantification of the content of oxygen in the blood is extremely important in clinical chemistry and other fields. Various optical methods have been investigated for the detection of dissolved oxygen concentration based on the dynamic quenching of fluorescent or phosphorescent materials. Electrochemical methods, however, are more attractive due to their high sensitivity, simplicity and inexpensive detection equipment. Thus, much attention and effort has been expended to developing electrochemical devices.

Biosensor history generally began in the early 1960s and the progenitor of the biosensor was an American scientist named L. C. Clark. Clark had studied the electrochemistry of oxygen reduction at platinum metal electrodes, pioneering the use of a platinum metal electrode as an oxygen sensor. In fact, platinum electrodes used to detect oxygen electrochemically are often referred to generically as "Clark electrodes."

U.S. Pat. No. 4,311,151 (1982, Hagihara) is one example of a well-known electrochemical oxygen sensor similar to the conventional Clark electrode. Hagihara discloses an oxygen measuring electrode assembly for transcutaneous measurement of the partial pressure of oxygen in arterial blood. The assembly includes an anode, a cathode that has a thin ring surface or circularly-bounded field of dot-shaped surfaces and an insulating electrode holder, a disposable tubular member holder fixedly holding the periphery of an oxygen permeable hydrophobic electrode membrane, and a skin-heating part including a heat-conducting block that is thermally connected to a heater and a temperature detector. Oxygen permeates through a gas permeable hydrophobic membrane from the blood sample into an internal electrolyte solution where it is reduced at the cathode. The oxygen reduction current, measured amperometrically, is proportional to the dissolved oxygen concentration.

Further development work of the "Clark" type electrode by J. W. Severinghaus et al. led to the development of a practical electrochemical oxygen sensor for clinical use.

Recently, P. D'Orazio et al. (Clinical Chemistry 43, 1804-1805, 1997) reported a planar amperometric oxygen sensor. A polymeric perfluorinated ionomer available from Sigma-Aldrich under the trademark Nafion® can be used as an internal electrolyte and is spin-coated along with a custom-made, patented polymer.

Potentiometric oxygen gas sensors have also been devised. U.S. Pat. No. 6,663,756 (2003, Lee et al.) discloses a microchip-based oxygen gas sensor based on differential potentiometry. The working electrode is a cobalt-plated electrode, a buffered hydrogel, and an ion selective gas-permeable membrane. The reference electrode is a silver chloride electrode with the same ion selective gas-permeable membrane. By taking advantage of the corrosion potential, the microchip-based oxygen gas sensor measures the content of dissolved oxygen in a sample solution.

Chemical sensors for clinical blood analysis have been widely studied. The theory and practice as well as history of electrochemical sensors for clinical measurement of blood gases were well reviewed by C. E. W. Hahn (Analyst, 123, 57R-86R, 1998). Previously reported oxygen sensors, however, require a relatively large volume of blood.

To be usable as a clinical sensor, the sensors should give an easy, accurate analysis of a sample and be economical. Point-of-care and high sensitivity are also required for allowing health care personnel to perform analysis with a small volume of blood, which is especially important for infant patients.

Therefore, what is needed is an oxygen sensor that can be used to measure dissolved oxygen accurately and precisely with a minimum quantity of sample volume. What is also needed is an oxygen sensor that is disposable.

SUMMARY OF INVENTION

It is an object of the present invention to provide an electrochemical oxygen sensor that measures dissolved oxygen accurately in a small amount of fluid sample. It is another object of the present invention to provide an amperometric oxygen sensor that measures dissolved oxygen accurately in a sample of about 0.5 µL or less. It is a further object of the present invention to provide an amperometric oxygen sensor that is easily manufactured. It is still another object of the present invention to provide an amperometric oxygen sensor that is disposable and that measures oxygen with high accuracy and precision.

The present invention achieves these and other objectives by providing an oxygen sensor that incorporates several embodiments including, but not limited to, either a 4-layer construction or 3-layer construction as disclosed in U.S. Pat. Nos. 6,767,441, 6,287,451, 6,258,229, 6,837,976, and U.S. Patent Publication No. 2003/0196894A1, all of which are incorporated herein by reference.

The present invention has a laminated, elongated body having a fluid sample channel connected between a fluid sample inlet on one end of the laminated body and a vent hole spaced from the inlet. Within the fluid sample channel lie at least one working electrode and a reference electrode. The arrangement of the working electrode and the reference electrode is not important for purposes of the results obtained from the sensor. The working electrode and the reference electrode are each in electrical contact with separate conductive paths. The separate conductive paths terminate on the end opposite the fluid sample inlet of the laminated body and are exposed for making an electrical connection to a reading device.

The laminated body has a bottom layer made from a plastic material. In one embodiment, several conductive paths are delineated on one side of the bottom layer. The conductive paths may be deposited on the bottom layer by screen printing, by vapor deposition, or by any method that provides for a conductive coating that adheres to the bottom layer. The conductive paths may be individually disposed on the bottom layer, or a conductive coating may be disposed on the bottom layer followed by etching/scribing the required number of conductive paths. The etching process may be accomplished chemically, mechanically scribing lines in the conductive layer, using a laser to scribe the conductive layer into separate conductive paths, or by any means that will cause a break between and among the separate conductive paths required for the electrodes of the present invention. Conductive coatings that may be used are coatings of copper, gold, tin oxide/gold, palladium, other noble metals or their oxides, or carbon film compositions. The preferred conductive coatings are gold film or a tin oxide/gold film composition.

In one embodiment of the present invention (4-layer construction), the laminated body has a first middle layer, also called a reagent holding/electrode area defining layer, on top of the bottom layer and the conductive paths. The first middle layer, or reagent holding layer, contains at least two openings that form wells for one or more working electrodes and a reference electrode when laminated to the bottom layer. Each opening corresponds to and exposes a small portion of a single conductive path. At least the working electrode wells hold a reagent matrix. When more than one working electrode is included, the openings for the working electrodes are substantially the same size or have a constant, known ratio. The opening for the reference electrode may be the same or different size as the openings for the working electrodes. The placement of all of the openings is such that they will be all positioned within the fluid sample channel described above. The reagent holding layer is also made of an insulating dielectric material, preferably plastic, and may be made by die cutting the material mechanically or with a laser and then adhering the material to the bottom layer. An adhesive, such as a pressure-sensitive adhesive, may be used to secure the reagent holding layer to the base layer. Adhesion may also be accomplished by ultrasonically bonding the reagent layer to the base layer. The reagent holding layer may also be made by screen printing an insulating material or by binding a photopolymer over the base layer.

The laminated body also has a second middle layer, also called a channel forming layer, on top of the reagent holding layer. The channel forming layer is also made of a plastic insulating material and creates the sample fluid channel of the laminated body. A U-shaped cutout is formed in one end of the channel forming layer. The U-shaped cutout overlays the electrode wells in the reagent holding layer with the open end forming the fluid sample inlet of the laminated body described earlier. A double coated, pressure-sensitive adhesive tape may be used as the channel forming layer.

The laminated body of the present invention has a cover with a vent opening and an optional inlet notch. The vent opening is located such that at least a portion of the vent opening overlays the bottom of the U-shaped cutout of the channel forming layer. The vent allows air within the fluid sample channel to escape as the fluid sample enters the sample inlet of the laminated body. The optional inlet notch is located at the sample inlet end. The fluid sample generally fills the fluid sample channel by capillary action. Capillary forces are enhanced by either using a hydrophilic material to form the cover, or by coating at least a portion of one side of a hydrophobic material with a hydrophilic substance in the area of the cover that faces the fluid sample channel between the sample inlet of the laminated body and the vent opening of the cover. It should be understood that an entire side of the cover may be coated with the hydrophilic substance and then bonded to the channel forming layer.

In the embodiments using a reagent holding layer (4-layer construction), one of the electrode wells contains electrode material (i.e. reagent matrix) for the working electrode (W) and one for the reference electrode (R). The positional arrangement of the working electrode and the reference electrode in the channel are not critical for obtaining usable results from the oxygen sensor. The possible electrode arrangements within the fluid sample channel may be W-R or R-W with the arrangement listed as the arrangement in which electrodes would appear from the open end of the laminated body to the vent opening. The preferred position was found to be W-R; that is, as the sample fluid enters the sample inlet of the laminated body, the fluid sample covers W first, then R. The working electrode and the reference electrode are each in electrical contact with separate conductive paths, respectively. The separate conductive paths terminate and are exposed for making an electrical connection to a reading device on the end opposite the sample inlet end of the laminated body.

The working electrode is loaded with an oxygen measuring reagent or mixture containing at least a redox mediator (preferably a reduced form of the redox mediator), an oxidase, and a peroxidase. The reagent mixture is dried to form a reagent matrix. The oxygen measuring reagent may optionally contain one or more of the following materials either alone or in combination. The optional materials include a surfactant, a polymer binder, an inactive bulking agent, and an antioxidant. The reference electrode may be loaded with the same mixture as the working electrode. It should be noted, however, that the reference electrode well could be loaded with a redox mediator (either reduced or oxidized form or combination) with or without a surfactant, a polymer binder, an inactive bulking agent, and an antioxidant. Alternatively, the reference electrode well could also be loaded with a Ag/AgCl layer (e.g. by applying Ag/AgCl ink or by sputter-coating a Ag or Ag/AgCl layer) or other reference electrode materials.

In the 3-layer embodiment, the three layers are the same or similar to those in the 4-layer construction except that it does not include a reagent holding layer. The U-shaped channel cutout is located at the sensor end (sample inlet end). The length, width and thickness of the U-shaped channel cutout define the capillary channel volume. The length and width of the U-shaped channel cutout along with the base conductive layer define the areas of the working and reference electrodes. The working electrode (W) and reference electrode (R) are preferably covered by the same reagent mixture.

The redox mediator is capable of transferring electrons between the enzyme-catalyzed reactions and the working electrode. The preferable mediators are redox chemicals in reduced form. The mediator used in the present invention may be at least one of a variety of chemicals in their reduced form, or virtually any oxidizable species or electron donors. Examples of usable compounds are potassium ferrocyanide $(K_4Fe(CN)_6)$, $[Fe(phen)_3]^{2+}$, $[Fe(bpy)_3]^{2+}$, $[Co(NH_3)]^{2+}$, $[Co(phen)_3]^{2+}$, $[Co(bpy)_3]^{2+}$, $[Os(bpy)_2Cl]^+$, $[Os(phen)_2Cl]^+$, $[Ru(bpy)_2]^{2+}$, $[Rh(bpy)_2]^{2+}$, cobalt phthalocyanine, various ferrocenes, methylene blue, methylene green, 7,7,8,8-tetracyanoquinodimethane, tetrathiafulvalene, toluidine blue, meldola blue, N-methylphenazine methosulfate, phenyldiamines, 3,3',5,5'-tetramethylbenzidine, pyrogallol, and benzoquinone where "phen" is 1,10-phenanthroline and "bpy" is 2,2'-bipyridine. It is desirable that the mediator is capable of being oxidized chemically by hydrogen peroxide resulting from the enzymatic reactions such as those described in Eqs. (1) and (2) below. It is further desirable that the oxidized form of the mediator is capable of being reduced electrochemically at the working electrodes at the applied potential. It is still further desirable that the mediator is stable in the matrix. The preferred mediator in the present invention is potassium ferrocyanide.

The oxidase is selected from those capable of producing hydrogen peroxide, such as, for example, glucose oxidase, acyl-CoA oxidase, N-acylhexosamine oxidase, D-amino acid oxidase, cholesterol oxidase, fructosyl-peptide oxidase, glutamate oxidase, L-α-glycerophosphate oxidase, lactate oxidase, putrescine oxidase, pyranose oxidase, pyruvate oxidase, sarcosine oxidase, uricase, xanthine oxidase, and the like. In the present invention, glucose oxidase is used.

The peroxidase may be from any source such as soybean (soybean peroxidase) or horseradish root (horseradish root peroxidase).

Surfactants may be selected from, but are not limited to, various anionic, cationic, non-ionic and zwitterionic detergents, such as Triton X-100, Tween 20, sodium cholate hydrate, hexadecylpyridinium cholide monohydrate, and CHAPs. The preferred surfactant in the present invention is Triton X-100.

Polymer binders may be selected from, but are not limited to, various water-soluble polymers, such as polyvinylpyrrolidone, polyethylene oxide, poly(vinyl alcohol), poly(ethylene glycol), poly(propylene glycol), polysulfone, carboxy methyl cellulose, hydroxypropyl cellulose, methyl cellulose, poly(2-ethyl-2oxazoline), and the like. The preferred polymer binders in the present invention is a combination of two polymer binders, polyethylene oxide and methylcellulose. The molecular weight of polyethylene oxide is in the range from thousands to millions. The preferred polyethylene oxide molecular weight is over 1 million, and, more preferably, it is about 4 million.

Antioxidants may be selected from, but are not limited to, various reductants and oxygen scavengers such as, for example, sodium sulfite, sodium hydrosulfite, hydrazine, hydroquinone, carbohydrazide, N,N-Diethylhydroxylamine, methylethylketoxime, biethylthreitol, erythorbic acid, and ascorbic acid. The preferred antioxidant in the present invention is sodium sulfite.

Bulking agents can be any compounds that do not react with any of the other ingredients within the reagent matrix and are inactive with the electrode surface. One class of bulking agents that meets these requirements are compounds such as sugars. Sugars can be selected from, but are not limited to, inactive sugars (i.e. not reacting with the enzymes or other ingredients used in the reagent mixture; not active at the electrode surface), such as trehalose, galactose, suctose, lactose, mannitol, mannose, fructose, sucrose, lactose, lactitol, sorbitol, and xylitol, maltose, and the like. The preferred bulking agent in the present invention is D(+) trehalose.

In the working electrode well, glucose in a sample is oxidized in the presence of GOD by dissolved oxygen when the sample enters the channel. The resulting products include gluconic acid and hydrogen oxide. The reaction equation is given below:

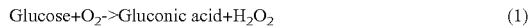

$$\text{Glucose} + O_2 \rightarrow \text{Gluconic acid} + H_2O_2 \quad (1)$$

The reduced form of ferrocyanide mediator, $[(Fe(CN)_6]^{4-}$, is capable of being oxidized to ferricyanide, $[(Fe(CN)_6]^{3-}$ in the presence of a peroxidase by hydrogen peroxide resulting from the above enzymatic reaction. When using ferrocyanide as the mediator, the oxidation reaction is as shown below:

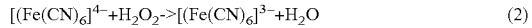

$$[(Fe(CN)_6]^{4-} + H_2O_2 \rightarrow [(Fe(CN)_6]^{3-} + H_2O \quad (2)$$

The oxidized form of the ferrocyanide ion (i.e. ferricyanide, $[(Fe(CN)_6]^{3-})$, is capable of being reduced electrochemically when an appropriate potential is applied to the working electrode. The resulting current signal is related to the glucose concentration as well as the oxygen concentration. Furthermore, if the glucose concentration is known, the oxygen concentration or $pO_2$ can be calculated. It is also desirable to use a potential where the electro-oxidation of other oxidizable interferents like ascorbic acid and acetaminophen either does not occur or is minimal. An example of such an applied potential is between about 0.0 V and about −0.6 V as measured against the reference electrode of the present invention. The preferred potential is about −0.3 V. This potential is preferred for providing a good ratio of signal versus background noise/interference.

The glucose concentration can be measured by a bench-top analyzer (e.g. YSI glucose analyzer), or by a hand-held glucose meter/strip (e.g. BD Logic). It should be pointed out that if other oxidase (e.g. lactate oxidase) instead of glucose oxidase is used in the working electrode reagent matrix, the corresponding substrate concentration (e.g. lactate concentration) should be measured by a bench-top analyzer, or by a hand-held meter/strip. It is also preferred to combine the oxygen sensor of the present invention with a glucose sensor (e.g., glucose strip), such that the oxygen concentration can be measure and calculated simultaneously using one drop or less of liquid sample. Such a combination can be done by either integrating the oxygen sensor of the present invention and the glucose sensor into one sample channel, or simply arranging the oxygen sensor of the present invention and the glucose sensor in a back-to-back arrangement or a side-by-side arrangement.

All of the advantages of the present invention will be made clearer upon review of the detailed description, drawings and appended claims.

BRIEF DESCRIPTION OF THE DRAWINGS

FIG. 1 is a perspective view of one embodiment of the present invention showing the test strip.

FIG. 2 is an exploded view of the embodiment in FIG. 1 showing the four component layers of the test strip.

FIG. 3 is a perspective view of another embodiment of the present invention showing the test strip.

FIG. 4 is an exploded view of the embodiment in FIG. 3 showing the three component layers of the test strip.

FIG. 5 is a perspective view of another embodiment of the present invention showing a combined sensor strip having the four layer construction with two working electrodes namely an oxygen electrode and an interferant-compensating electrode.

FIG. 6 is an exploded view of the embodiment in FIG. 5 showing the arrangement of the component layers that includes an oxygen electrode and an interferant-compensating electrode.

DETAILED DESCRIPTION OF THE PREFERRED EMBODIMENT

Figure 7:
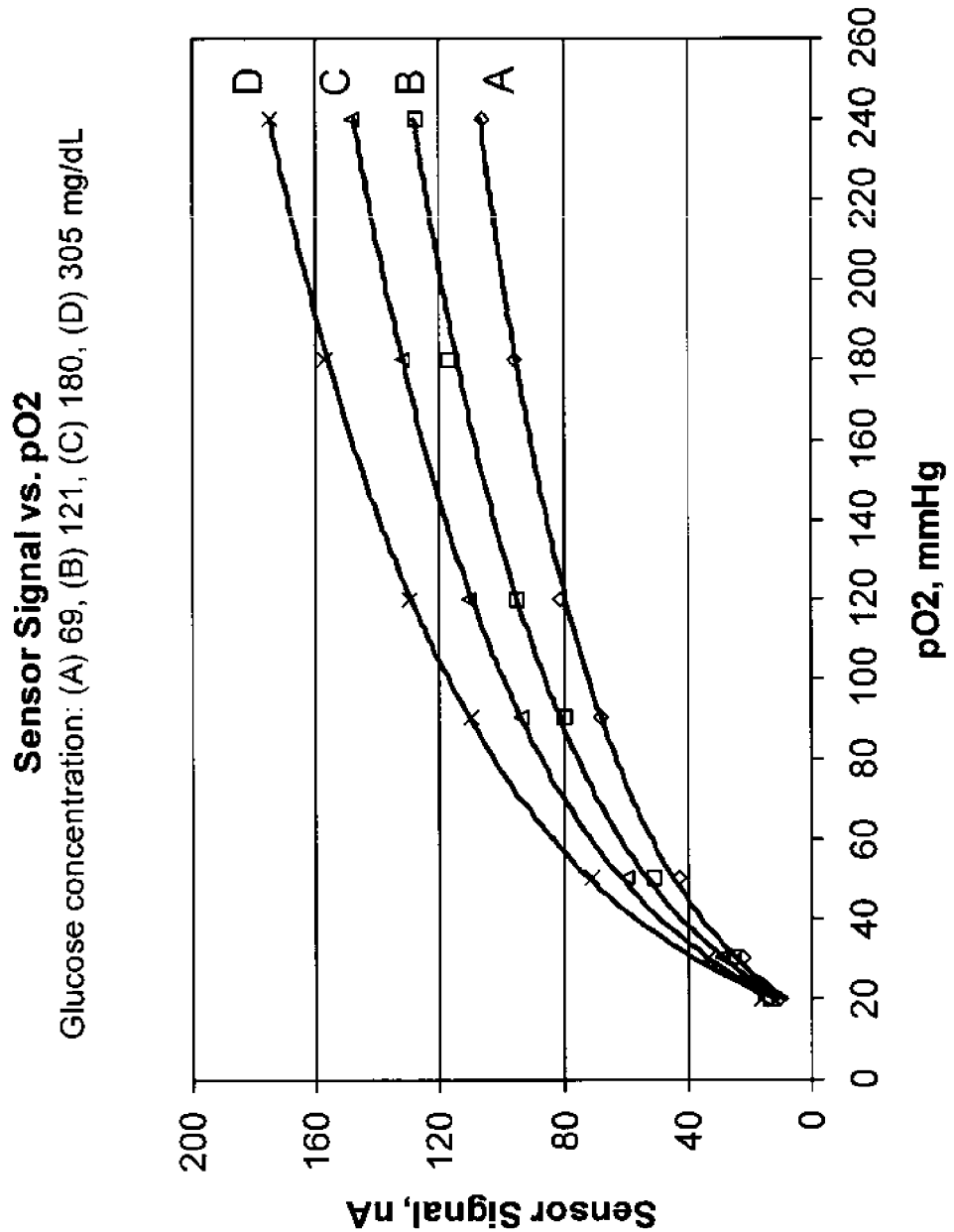
FIG. 7 shows the correlation between the sensor signal and the oxygen concentration.

The preferred embodiments of the present invention are illustrated in FIGS. 1-10. The oxygen sensor of the present invention can be made using either a 4-layer construction (FIG. 1) or a 3-layer construction (FIG. 3). The 4-layer construction has the same three layers as the 3-layer construction plus an additional reagent holding layer between a base/bottom layer and a channel forming layer.

Turning now to FIG. 1, the oxygen sensor 10 has a laminated body 12, a fluid sampling end 14, an electrical contact end 16, and a vent opening 52. Fluid sampling end 14 includes a fluid sample channel 17 between a fluid sample inlet 18 and vent opening 52. Electrical contact end 16 has three discrete conductive contacts 16a, 16b and 16c.

Turning now to FIG. 2, laminated body 12 includes a bottom layer 20, a reagent holding layer 30, a channel forming layer 40, and a cover 50. All layers of laminated body 12 are made of a dielectric material, preferably plastic. Examples of a preferred dielectric material are polyvinyl chloride, polycarbonate, polysulfone, nylon, polyurethane, cellulose nitrate, cellulose propionate, cellulose acetate, cellulose acetate butyrate, polyester, polyimide, polypropylene, polyethylene, polystyrene, and the like.

Bottom layer 20 has a conductive layer 21 on which is delineated to at least two conductive paths 22 and 24. The conductive paths 22, 24 may be formed by scribing or scoring conductive layer 21, or by silk-screening conductive paths 22, 24 onto bottom layer 20. Bottom layer 20 may also have a third conductive path 26 for incorporating another working electrode or other sensor combination that will be described later. Scribing or scoring of conductive layer 21 may be done by mechanically scribing the conductive layer 21 sufficiently to create at least two independent conductive paths 22, 24. The preferred scribing or scoring method of the present invention is done by using a carbon dioxide laser, a YAG laser or an eximer laser. Conductive layer 21 may be made of any electrically conductive material such as, for example, copper, gold, tin oxide/gold, palladium, other noble metals or their oxides, or carbon film compositions. The preferred electrically conductive material is gold or tin oxide/gold. A usable material for bottom layer 20 is a tin oxide/gold polyester film (Cat. No. FM-1) or a gold polyester film (Cat. No. FM-2) sold by Courtaulds Performance Films, Canoga Park, Calif.

In the embodiments using a reagent holding layer 30 (4-layer construction), reagent holding layer 30 has at least two reagent holding openings 32 and 34. Reagent holding opening 32 exposes a portion of conductive path 22 and reagent holding opening 34 exposes a portion of conductive path 24 creating reagent holding wells. Reagent holding layer 30 is made of a plastic material, preferably a medical grade one-sided adhesive tape available from Adhesive Research, Inc., of Glen Rock, Pa. Acceptable thicknesses of the tape for use in the present invention are in the range of about 0.001 in. (0.025 mm) to about 0.005 in. (0.13 mm). One such tape, Arcare® 7815 (about 0.003 in. (0.075 mm)), is preferred due to its ease of handling and good performance in terms of its ability to hold a sufficient quantity of chemical reagents and to promote capillary action through the fluid sample channel of the sensor. It should be understood that the use of a tape is not required. Reagent holding layer 30 may be made from a plastic sheet and may be coated with a pressure sensitive adhesive, a photopolymer, ultrasonically-bonded to base layer 20, or silk-screened onto base layer 20 to achieve the same results as using the polyester tape mentioned.

The two reagent holding openings 32, 34 define electrode areas W and R, respectively, and hold chemical reagents forming one working electrode and one reference electrode. Generally, electrode area W is loaded with a reagent matrix that contains an oxidase, a redox mediator (preferably a reduced form of the redox mediator) and a peroxidase. One or more chemical components such as polymers, surfactants, bulking agents, and antioxidants may be optionally included in the reagent matrix. A reference reagent matrix may be loaded in electrode area R that is similar to the oxygen reagent matrix.

Typically, electrode area R must be loaded with a redox reagent or mediator to make the reference electrode function when using the preferred conductive coating material. If R is not loaded with a redox reagent or mediator, working electrode W will not function properly. Alternatively, the reference electrode (electrode area R) could be loaded with a Ag/AgCl layer (e.g. by applying Ag/AgCl ink or by sputter-coating a Ag or Ag/AgCl layer) or other reference electrode materials that do not require a redox mediator to function properly.

The size of the reagent holding openings is preferred to be made as small as possible in order to make the fluid sample channel of the oxygen sensor as short as possible while still being capable of holding sufficient chemical reagent to function properly. The preferred shape of the reagent holding openings is round and has a preferred diameter of about 0.03 in. (0.75 mm). The two reagent holding openings 32, 34 are aligned with each other and are spaced about 0.0256 in. (0.65 mm) from each other. The circular reagent holding openings are for illustrative purposes only. It should be understood that the shape of the reagent holding openings is not critical and that the size of the openings is driven more by the technical feasibility of dispensing the reagent matrix mixture into the openings and other manufacturing limitations.

The positional arrangement of the working electrode and the reference electrode in the channel is not critical for obtaining usable results from the oxygen sensor. The possible electrode arrangements within the sample fluid channel may be W-R or R-W, with the arrangement listed as the arrangement of electrodes would appear from the sample inlet 18 of laminated body 12 to the vent opening 52. The preferred position was found to be W-R; that is, as the fluid sample enters sampling end 14 of laminated body 12, the fluid sample would cover W first, then R. Such an arrangement may be beneficial for obtaining usable results when the sample is insufficient or partially insufficient.

The working electrode and the reference electrode are each in electric contact with separate conductive paths. The separate conductive paths terminate and are exposed for making an electric connection to a reading device on the end opposite the sample inlet 18 of laminated body 12.

In the embodiments using reagent holding layer 30 (4-layer construction), channel forming layer 40 has a U-shaped cutout 42 located at the fluid sampling end 14. The length of cutout 42 is such that when channel forming layer 40 is laminated to reagent holding layer 30, electrode areas W and R are within the space defined by cutout 42. The length, width and thickness of the U-shaped cutout 42 define the capillary channel volume. Channel forming layer 40 is made of a plastic material, preferably a medical grade double-sided pressure sensitive adhesive tape available from Adhesive Research, Inc., of Glen Rock, Pa. Acceptable thicknesses of the tape for use in the present invention are in the range of about 0.001 in. (0.025 mm) to about 0.010 in. (0.25 mm). One such tape is Arcare® 7840 (about 0.0035 in. (0.089 mm)). U-shaped cutout 42 can be made with a laser or by die-cutting. The preferred method is to die-cut the U-shaped cutout. The preferred size of the U-shaped cutout is about 0.155 in. long (3.94 mm), about 0.05 in. wide (1.27 mm) and about 0.0035 in. thick (0.089 mm).

Cover 50, which is laminated to channel forming layer 40, has vent opening 52 spaced from the fluid sampling end 14 of oxygen sensor 10 to insure that the fluid sample in the fluid channel 17 will completely cover electrode areas W and R. Vent opening 52 is positioned in cover 50 so that it will align somewhat with U-shaped cutout 42. Preferably, vent opening 52 will expose a portion of and partially overlay the bottom of the U-shaped cutout 42. Although the preferable shape of vent hole 52 is a rectangle with dimensions of about 0.08 in. (2 mm) by about 0.035 in. (0.9 mm), any shape would provide a similar venting function. Preferably, cover 50 also has an inlet notch 54 at fluid sampling end 14 to facilitate transporting of the fluid sample into the fluid sample channel 17 at the sample inlet 18. The preferred shape is a half circle, which is located approximately in the middle of the channel entrance. The preferred size is that of a circle with a diameter of about 0.028 in. (0.71 mm). The preferred material for cover 50 is a polyester film. In order to facilitate the capillary action, it is desirable for the polyester film to have a highly hydrophilic surface that faces the capillary channel. Transparency films (Cat. No. PP2200 or PP2500) from 3M are the preferred material used as the cover in the present invention.

FIG. 3 illustrates a 3-layer oxygen sensor 10'. Like the 4-layer embodiment, oxygen sensor 10' has a laminated body 12, a fluid sampling end 14, an electrical contact end 16, and a vent opening 52. Fluid sampling end 14 includes a fluid sample channel 17 between a sampling end inlet 18 and vent opening 52. Electrical contact end 16 has three discrete conductive contacts 16a, 16b and 16c.

As can be seen from FIG. 4, laminated body 12 is composed of a bottom layer 20, a channel forming layer 40 with an optional inlet notch 54, and a cover 50. As noted earlier, all layers of laminated body 12 are made of a dielectric material, preferably plastic. Unlike the 4-layer embodiment, there is no separate reagent holding layer in the 3-layer embodiment. Channel forming layer 40 also delineates the area in which a pre-determined amount of reagent matrix is disposed.

Another embodiment of the combination sensor is illustrated in FIGS. 5 and 6. FIG. 5 shows an interferant-compensated oxygen sensor 500 with a laminated body 512, a fluid sampling end 514, an electrical contact end 516 and a vent opening 552. Fluid sampling end 514 includes a sample fluid channel 517 between sample inlet 518 and vent opening 552.

FIG. 6 shows an expanded view of laminated body 512 of the embodiment in FIG. 5. Laminated body 512 has a bottom layer 520, a reagent holding layer 530, a channel forming layer 540 having a U-shaped cutout 542, and a cover 550. Bottom layer 520 has a conductive layer 521 on which is delineated at least three conductive paths 522, 524 and 526. Reagent holding layer 530 has at least three reagent holding openings 532, 534 and 536. Reagent holding opening 532 exposes a portion of conductive path 522, reagent holding opening 534 exposes a portion of conductive path 524 and reagent holding opening 536 exposes a portion of conductive path 526, all creating respective electrode wells.

The three reagent holding openings 532, 534 and 536 define electrode areas W1, W2 and R, respectively, and hold chemical reagents forming a first working electrode, a second working electrode and one reference electrode. Generally, electrode area W2 is loaded with an oxygen reagent matrix that includes an oxidase, a redox mediator (preferably a reduced form of the redox mediator) and a peroxidase. Electrode area W1 is loaded with an interferant-correcting reagent matrix similar to the reagent matrix in W2 but without the oxidase. A reference reagent matrix may be loaded in electrode area R that is similar to either the oxygen reagent matrix or the interferant-correcting reagent matrix. It should be noted that the positional arrangement of the two working electrodes and the reference electrode in the channel are not critical for obtaining usable results from the oxygen correcting sensor combination.

Typically, electrode area R must be loaded with a redox reagent or mediator to make the reference electrode function when using the preferred conductive coating material. If R is not loaded with a redox reagent or mediator, the working electrodes W1, W2 will not function properly. Alternatively, the reference electrode (electrode area R) may be loaded with a Ag/AgCl layer (e.g. by applying Ag/AgCl ink or by sputter-coating a Ag or Ag/AgCl layer) or other reference electrode materials that do not require a redox mediator to function properly with the working electrodes.

In addition to measuring the fluid sample resistance between electrode area W1 and the reference electrode to compensate the sensor readings for blood hematocrit, oxidizable interferants such as ascorbic acid, uric acid and acetaminophen, to name a few, (which also cause inaccurate readings in the output of an electrochemical biosensor), can also be measured to compensate the sensor readings for these interferants. The interferant effect can be negated by subtracting the current response at W1 (first working electrode) from the current response from W2 (second working electrode) to calculate the analyte concentration in the sample fluid. This is achieved by maintaining the surface area of W1 substantially equal to the surface area of W2 or with a known ratio. Also important is the composition of the reagents disposed on W1 and W2. The reagents are designed to have a minimal effect on the response of the interferences which also contributes to the accuracy of the analyte measurement.

It should be understood that the first working electrode may also be configured to measure the glucose concentration instead of being used to correct for the presence of interferants, or an additional electrode may be incorporated into the sensor strip to include both a glucose measuring electrode and an interferant correcting electrode.

Assembly of the various embodiments of the present invention is relatively straightforward. For the 4-layer configuration, the bottom layer and reagent holding layer are laminated to each other followed by dispensing the reagent mixture into the reagent holding openings. After drying the reagent mixture, the channel forming layer is laminated onto the reagent holding layer and the cover is then laminated onto the channel forming layer. For the 3-layer construction, the bottom layer and the channel forming layer are laminated to each other followed by dispensing the reagent mixture into the U-shaped channel. After drying the reagent mixture, the cover is then laminated onto the channel forming layer.

The reagent mixture for the oxygen sensor includes at least an oxidase, a reduced form of a redox mediator and a peroxidase. The reagent mixture may optionally include one or more of a polymer, a surfactant, an inactive bulking agent, and an antioxidant.

The redox mediator may be any inorganic or organic redox species. Examples of usable redox mediators are potassium ferrocyanide, $[Fe(phen)_3]^{2+}$, $[Fe(bpy)_3]^{2+}$, $[Co(NH_3)]^{2+}$, $[Co(phen)_3]^{2+}$, $[Co(bpy)_3]^{2+}$, $[Os(bpy)_2Cl]^+$, $[Os(phen)_2Cl]^+$, $[Ru(bpy)_2]^{2+}$, $[Rh(bpy)_2]^{2+}$, cobalt phthalocyanine, various ferrocenes, methylene blue, methylene green, 7,7,8,8-tetracyanoquinodimethane, tetrathiafulvalene, toluidine blue, meldola blue, N-methylphenazine methosulfate, phenyldiamines, 3,3',5,5'-tetramethylbenzidine, pyrogallol, and benzoquinone where "phen" is 1,10-phenanthroline and "bpy" is 2,2'-bipyridine.

It is preferred that the mediator is capable of being oxidized chemically by hydrogen peroxide resulting from enzymatic reactions such as those illustrated in Eqs. (1) and (2) above. It is further desirable that the oxidized form of the mediator is capable of being reduced electrochemically at the working electrodes at the applied potential. It is still further desirable that the mediator is stable in the matrix. It is also desirable that the mediator can make the reference function properly. The preferred mediator in the present invention is potassium ferrocyanide ($K_4Fe(CN)_6$). The concentration of potassium ferrocyanide in the reagent mixture is preferably in a range of about 0.1% (W/W) to about 10%. More preferably, the concentration of potassium ferrocyanide is about 1%. Reagent mixture as used in this specification means the reagent mixture before drying and forming the reagent matrix.

The polymers used as binders should be sufficiently water-soluble and should also be capable of stabilizing and binding all other chemicals in the reagent mixture in electrode areas W and R to the conductive surface coating. Examples of useful polymer binders include various water-soluble polymers, such as polyvinylpyrrolidone, polyethylene oxide, poly(vinyl alcohol), poly(ethylene glycol), poly(propylene glycol), polysulfone, carboxy methyl cellulose, hydroxypropyl cellulose, methyl cellulose, poly(2-ethyl-2oxazoline), and the like. Although one or more polymer binders can be used in the reagent matrix, the preferred embodiment of the present invention uses two polymer binders as the reagent matrix binder. One of the preferred polymer binders is polyethylene oxide. Its molecular weight ranges from thousands to millions. Preferably, the molecular weight is over 1 million. More preferably, the molecular weight is about 4 million. The preferred polyethylene oxide is a product available from Scientific Polymer Products, NY, USA (MW 4,000,000, Cat No. 344). The concentration of polyethylene oxide in the reagent mixture is preferably in a range of about 0.04% (W/W) to about 2%. More preferably, the concentration of polyethylene oxide is about 0.4%.

The second polymer binder is preferably methyl cellulose, which is available under the brand name of Methocel 60 HG (Cat. No. 64655, Fluka Chemicals, Milwaukee, Wis., USA). The concentration of methyl cellulose in the reagent mixture is preferably in a range of about 0.05% (W/W) to about 5%. More preferably, the concentration of methyl cellulose is about 0.75%.

To stabilize the reduced form of the redox mediator, a small amount of an antioxidant is preferably added to the reagent mixture. The addition of a small amount of antioxidant to the reagent mixture provides for a long-term shelf life. The antioxidant must not interfere with the enzymatic reactions and the ensuing amperometric measurement. Antioxidants can be selected from, but are not limited to, various reductants and oxygen scavengers, such as sodium sulfite, sodium hydrosulfite, hydrazine, hydroquinone, carbohydrazide, N,N-Diethylhydroxylamine, methylethylketoxime, diethylthreitol, erythorbic acid, ascorbic acid. The preferred antioxidant in the present invention is sodium sulfite and is available from most chemical supply companies. The concentration of antioxidant in the reagent mixture is preferably in a range of about 0.01% (W/W) to about 1%. More preferably, the concentration of antioxidant is about 0.1%.

The optional surfactant facilitates dispensing of the reagent mixture into the reagent openings for the working and reference electrodes as well as for quickly dissolving the dry chemical reagents. The amount and type of surfactant is selected to assure the previously mentioned function and to avoid a denaturing effect on the enzymes. Surfactants can be selected from, but are not limited to, various anionic, cationic, non-ionic and zwitterionic detergents. Examples of surfactants include chemicals such as Triton X-100, Tween 20, sodium cholate hydrate, hexadecylpyridinium cholide monohydrate, CHAPs. The preferred surfactant is a polyoxyethylene ether. More preferably, it is t-octylphenoxypolyethoxyethanol and is available under the brand name Triton X-100. The concentration of surfactant in the reagent mixture is preferably in a range of about 0.01% (W/W) to about 2%. More preferably, the concentration of surfactant is about 0.4%.

A water soluble and inactive ingredient or bulking agent is preferably added into the reagent mixture to help prevent bubble entrapment at the electrode openings when a fluid sample fills the capillary channel. The bulking agent also should not react with other ingredients in the reagent mixture and should be inactive at the electrode surface. Examples of acceptable bulking agents include various sugars such as, for example, trehalose, galactose, sucrose, lactose, mannitol, mannose, fructose, sucrose, lactose, lactitol, sorbitol, and xylitol maltose, and the like. The preferred sugar is D(+) trehalose. The concentration of bulking agent in the reagent mixture is preferably in a range of about 0.5% (W/W) to about 25%. More preferably, the concentration of bulking agent is about 5%.

At least one oxidase must be included in the reagent matrix in order to produce hydrogen peroxide. The oxidase is selected from those capable of producing hydrogen peroxide such as, for example, glucose oxidase, acyl-CoA oxidase, N-acylhexosamine oxidase, D-amino acid oxidase, cholesterol oxidase, fructosyl-peptide oxidase, glutamate oxidase, L-α-glycerophosphate oxidase, lactate oxidase, putrescine oxidase, pyranose oxidase, pyruvate oxidase, sarcosine oxidase, uricase, and xanthine oxidase. In the present invention, glucose oxidase (about 260 units per mg, Cat. No. GO3AC, Genzyme, USA) is used for illustration purposes. Any other oxidase may be used as long as the corresponding substrate concentration can be easily measured. The concentration of oxidase in the preferred reagent mixture is preferably in a range of about 0.05% (W/W) to about 1.5%. More preferably, the concentration of oxidase is about 0.24%.

Peroxidase is used to catalyze the reaction of hydrogen peroxide resulting from the enzymatic reaction with the reduced form of the redox mediator, ferrocyanide. Peroxidase may be from any source such as soybean (soybean peroxidase) or horseradish root (horseradish root peroxidase). The preferred peroxidase used in the present invention is horseradish root peroxidase (about 126 units per mg, Cat. No. PEO 301) and is available from TOYOBO (Japan). The concentration of peroxidase in the reagent mixture is preferably in a range of about 0.1% (W/W) to about 3%. More preferably, the concentration of peroxidase is about 0.48%.

Accordingly, the preferred reagent mixture of the present invention contains about 0.75% (W/W) methyl cellulose (Methocel 60 HG), about 0.4% (W/W) polyethylene oxide, about 5% (W/W) bulking agent (D-(+) trehalose), about 0.4% (W/W) surfactant (Triton X-100), about 0.1% (W/W) antioxidant (sodium sulfite), about 1% (W/W) of the reduced form of a redox mediator (potassium ferrocyanide), about 0.24% (W/W) oxidase (glucose oxidase) (about 624 units per mL reagent mixture), and about 0.48% (W/W) peroxidase (horseradish root peroxidase) (about 605 units per mL reagent mixture).

Preparation of the Reagent Mixture

The reagent mixture is prepared in two steps:

Step 1: Into 100 ml of water, add 0.75 g Methocel 60 HG, 0.4 g polyethylene oxide, 5 g D-(+) trehalose, and 0.4 g Triton X-100. Stir the solution for 20 hrs.

Step 2: Into the above solution, add 0.1 g sodium sulfite, 1 g potassium ferrocyanide, 0.24 g glucose oxidase, and 0.48 g horseradish root peroxidase. Stir the solution for 10 min. The resulting solution is ready for dispensing.

Making of the Oxygen Sensor

For the 4-layer construction, about 60-100 nL of the reagent mixture is dispensed into one of the reagent holding openings, the same amount of the reagent mixture is dispensed into the other reagent holding opening. For the 3-layer construction, about 1-3 µL of the reagent mixture is dispensed into the U-shaped channel that covers both working and reference electrode areas.

After the addition of the reagents to the electrode areas, the device is dried on a hot plate at a temperature of about 35-45° C. for about 0.5-2 minutes. It is noted that drying out of the reagent mixture can be accomplished at room temperature or any temperature that does not affect the characteristics of the components of the reagent mixture. For the 4-layer construction, after drying, the channel forming layer along with the cover is laminated onto the reagent holding layer. For the 3-layer construction, the cover is laminated onto the channel forming layer.

Although the description of electrode construction above describes construction for a single sensor, the design and materials used are ideal for making multiple sensors from one piece of each layer material. This would be accomplished by starting with a relatively large piece of base layer having a conducting layer thereon. A plurality of scored lines are made into the conductive layer such that a repetitive pattern is created using the preferred scribing method previously described whereby each pattern will eventually define the conductive paths for each sensor. For the 4-layer construction, a large piece of the reagent holding layer material also having a plurality of openings in a repetitive pattern is sized to fit over the bottom layer in such a way that a plurality of sensors will be had when completed. The size of each aperture and the electrode material disposed in the plurality of electrode areas W and R are similar to that disclosed above.

After disposing the reagent mixture in their respective reagent holding openings and dried, a large piece of the channel forming layer material having a plurality of elongated apertures is layered onto the reagent holding layer material such that each elongated aperture of the channel forming layer material contains corresponding openings of the reagent holding layer material. A comparably-sized cover layer material having a plurality of vent openings and notches in a repetitive pattern is layered onto the channel forming layer material. The laminated sheet is then cut in appropriate locations to form individual oxygen sensors.

For the 3-layer construction, a large piece of the channel forming layer material having a plurality of elongated apertures is layered onto the bottom layer. After disposing the reagent mixture into the plurality of elongated apertures and dried, a comparably-sized cover layer material having a plurality of vent openings and notches in a repetitive pattern is layered onto the channel forming layer material. The laminated sheet is then cut in appropriate locations to form individual oxygen sensors.

Testing of the Oxygen Sensor

When a fluid sample is applied to a single strip of the present invention, the fluid sample enters the channel through the sample inlet and flows over the working and reference electrodes and stops at the threshold of the vent opening.

Chronoamperometry (i-t curve) was used to measure the current response of the oxygen sensors using an Electrochemical Analyzer (Model 812, CH Instruments, Austin, Tex., USA). Oxygen concentration ($pO_2$) was controlled using a Tonometer (Precision Gas Mixer, PGM-3, Medicor, Inc., Salt Lake City, Utah, USA). Two milliliters of the blood sample were placed into a temperature-controlled (37° C.) cylindrical rotating cuvette and tonometered for 15 minutes.

Once a blood sample entered the sensor, a potential of −0.3 Volts was applied across the working and the reference electrodes. The resultant current signals arising from the reduction of the oxidized form of the redox mediator are attributed to both oxygen concentration ($pO_2$) and glucose concentration in the blood sample. If not stated otherwise, the current at 20 seconds was recorded. The glucose concentration of the same blood sample was measured with a YSI glucose analyzer (Model 2300 Stat Plus, YSI Inc., Yellow Spring, Ohio).

The following examples illustrate the unique features of the present invention using a sensor having the 4-layer construction.

EXAMPLE 1

Demonstration of Linear Range

Blood samples with different oxygen concentrations and different glucose concentrations were tested with the oxygen sensor of the present invention in connection with the Electrochemical Analyzer (CH Instruments, Model 812, Austin, Tex., USA). FIG. 7 shows the measured current response in nanoamperes of the oxygen sensors of the present invention to varying oxygen concentrations in the blood samples at four glucose concentrations, respectively.

As seen from the graph, the sensors of the present invention respond to the oxygen concentration in the blood samples over a range of about 20 to about 240 mmHg. Note that the responses are also dependent on the glucose concentration. Generally, the oxygen concentration can be expressed as a function of the current response and the glucose concentration as:

$$pO_2 = f(i,c) \quad (3)$$

Where i is the current in nanoamps c is the glucose concentration

The relationship among the oxygen concentration ($pO_2$, mmHg), glucose concentration and the current response for the particular oxygen sensor configuration used in the examples was determined from the empirical data to be $$pO_2 = ai^2 + bi + k_1 \quad (4)$$

Where i is the current in nA; a and b are constants at a given glucose concentration defined by the following equations and $k_1$ equals 19.5.

$$a = 2 \times 10^{-7} C^2 - 9 \times 10^{-05} C + k_2 \quad (5)$$

$$b = 2 \times 10^{-6} C^2 - k_3 C + k_4 \quad (6)$$

Where C is the glucose concentration; $k_2$ equals 0.0172; $k_3$ equals 0.0015; $k_4$ equals 0.3739 for the particular configuration and sizing of the electrodes tested.

It should be understood that the constants are empirical constants based on data obtained from electrodes having certain size and dimension configurations and that changing the configuration of the spacing, surface area and size of the electrodes will change the constant values. These new values again would be determined by the empirical data for those electrodes.

Therefore, based on the testing results (current response and glucose concentration), the oxygen concentration ($pO_2$) can be easily calculated from Equations (4), (5) and (6).

Figure 8:
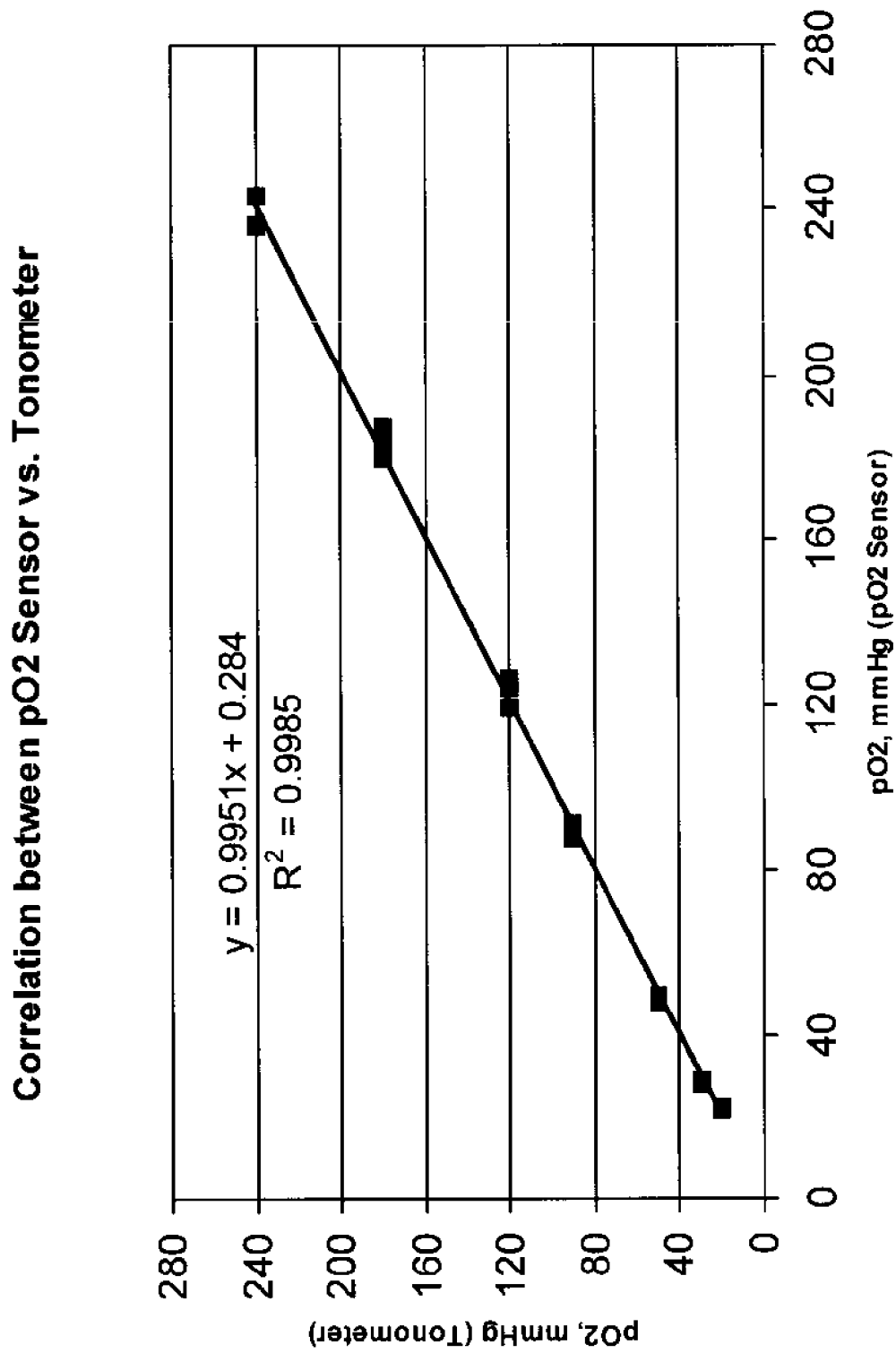
FIG. 8 shows the correlation between the oxygen sensor and tonometered oxygen.
Figure 9:
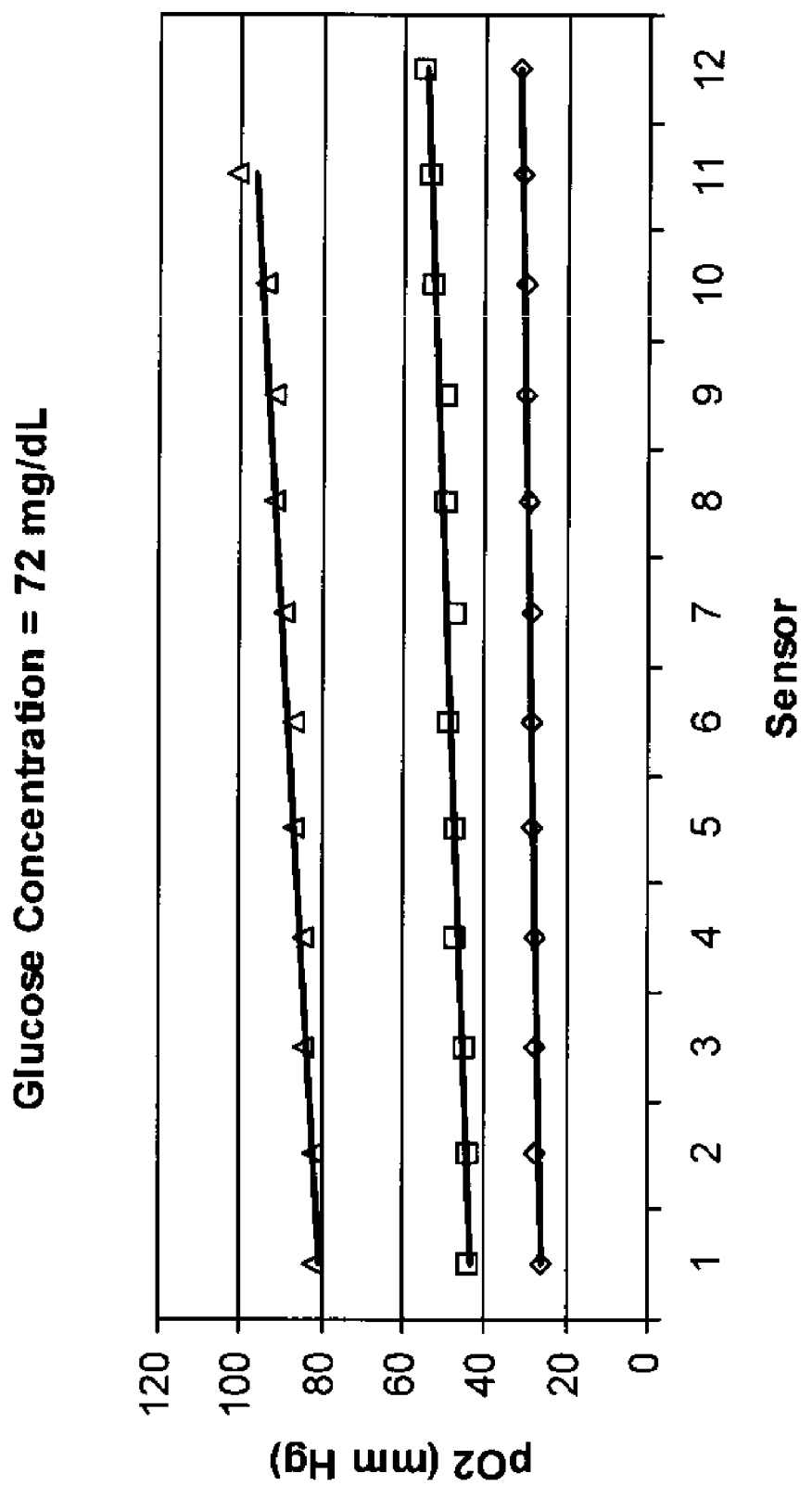
FIG. 9 is an graphical illustration of the precision of the oxygen sensor of the present invention at various oxygen concentrations at one glucose concentration.
Figure 10:
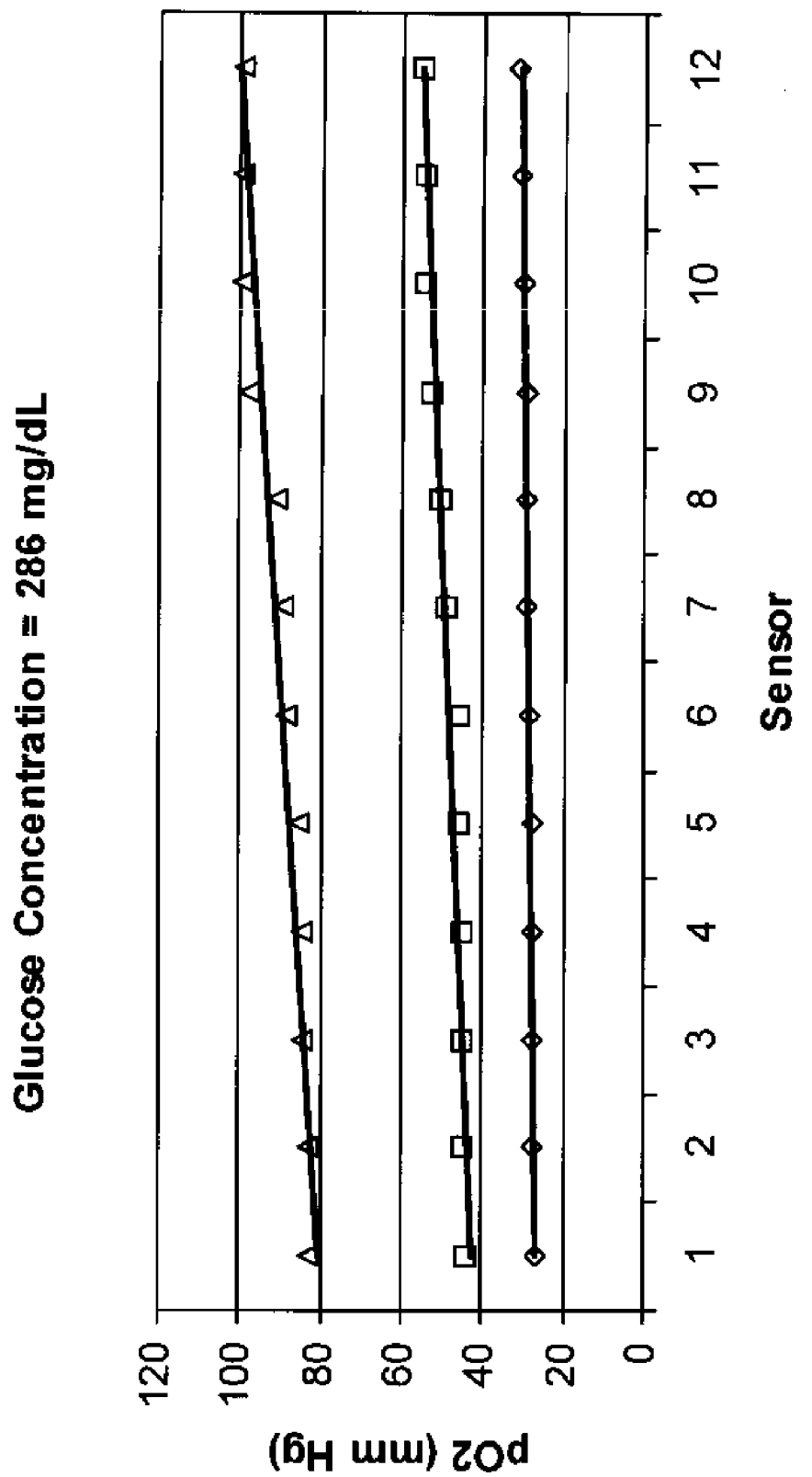
FIG. 10 is an graphical illustration of the precision of the oxygen sensor of the present invention at various oxygen concentrations at another glucose concentration.

FIG. 8 shows the correlation between the preferred 4-layer oxygen sensors of the present invention and tonometered oxygen over an oxygen range of about 20 to about 240 mmHg. The regression equation is $$pO_2(\text{Tonometer}) = 0.9951 \, pO_2(\text{sensor}) + 0.284 \quad (5)$$

with a square regression constant ($R^2$) of 0.9985. The results indicate that the oxygen sensors respond to the oxygen concentration accurately.

EXAMPLE 2

Demonstration of Precision of Sensors

The precision of the sensors of the present invention was investigated at three oxygen concentrations (30, 50 and 90 mmHg) for each of two glucose concentrations (72 and 286 mg/dL). The results are summarized in the Table 1 and illustrated if FIGS. 9 and 10. Typically, the coefficient of variation (CV, %) was found to be in the range of about 5.4 to about 8.5.

TABLE 1

| | Glucose Concentration, mg/dL | | | | | |
|---|---|---|---|---|---|---|
| | 72 | | | 286 | | |
| $pO_2$, mmHg | 30 | 50 | 90 | 30 | 50 | 90 |
| $pO_2$ Sensor Result | 26.1 | 44.1 | 82.5 | 26.6 | 44.5 | 83.0 |
| | 27.4 | 44.1 | 82.5 | 27.4 | 45.2 | 83.0 |
| | 27.4 | 45.2 | 84.6 | 27.4 | 45.2 | 84.3 |
| | 27.4 | 47.6 | 84.6 | 27.8 | 45.2 | 84.3 |
| | 28.8 | 47.6 | 86.8 | 27.8 | 45.9 | 85.6 |
| | 28.8 | 48.8 | 86.8 | 28.2 | 45.9 | 88.2 |
| | 28.8 | 47.6 | 89.0 | 29.1 | 48.8 | 89.5 |
| | 29.5 | 50.0 | 91.2 | 29.1 | 50.3 | 90.9 |
| | 30.3 | 50.0 | 91.2 | 29.1 | 52.6 | 98.1 |
| | 30.3 | 52.6 | 93.6 | 30.0 | 54.3 | 99.6 |
| | 31.1 | 53.9 | 100.9 | 30.9 | 54.3 | 99.6 |
| | 31.8 | 55.3 | 100.9 | 31.9 | 55.1 | 99.6 |
| Mean, mmHg | 29.0 | 48.9 | 89.6 | 28.8 | 48.9 | 90.5 |
| CV, % | 5.9 | 7.5 | 7.1 | 5.4 | 8.5 | 7.6 |

What is claimed is:

1. A method of determining the concentration of oxygen in a biological sample, said method comprising:
   using an oxygen sensor comprising a working electrode, a reference electrode and a reagent matrix disposed on at least said working electrode wherein said reagent matrix contains a reduced form of a redox mediator, an oxidase and a peroxidase to obtain an initial oxygen measurement and wherein said oxygen sensor has a known correlation between oxygen and a predefined analyte expressed as a function of the response of said oxygen sensor to both oxygen and said predefined analyte wherein said oxidase is a substrate of said predefined analyte;
   determining an analyte concentration of said biological sample wherein said analyte concentration is a substrate of said oxidase; and
   determining said concentration of oxygen in said biological sample using said determined analyte concentration and said initial oxygen measurement.

2. The method of claim 1 wherein said oxygen sensor using step further includes determining an oxygen empirical equation based on empirical data obtained with said oxygen sensor.

3. The method of claim 2 wherein said oxygen empirical equation is represented by the formula $pO_2=ai^2+bi+k_1$ where a and b are empirical constants at a given glucose concentration in milligrams per deciliter determined by the configuration of said oxygen sensor, $K_1$ is an empirical constant based on electrode configuration, and i is the current in nanoamps measured by said oxygen sensor.

4. The method of claim 1 further comprising fabricating said oxygen sensor by laminating a bottom layer, a channel forming layer and a cover forming a laminated body having a fluid sample inlet on one end, a substantially flat sample chamber in communication with said fluid sample inlet, said sample chamber being adapted to collect a fluid sample through said fluid sample inlet, and electrical contacts on the other end wherein said working electrode and said reference electrode are within said sample chamber.

5. The method of claim 4 further comprising laminating a reagent holding layer between said bottom layer and said channel forming layer.

6. The method of claim 1 further comprising fabricating said reagent matrix by selecting said reduced form of said redox mediator from redox mediators capable of being oxidized by hydrogen peroxide.

7. The method of claim 6 further comprising fabricating said reagent matrix by selecting said reduced form of said redox mediator from the group consisting of potassium ferrocyanide, $[Fe(phen)_3]^{2+}$, $[Fe(bpy)_3]^{2+}$, $[Co(NH_3)]^{2+}$, $[Co(phen)_3]^{2+}$, $[Co(bpy)_3]^{2+}$, $[Os(bpy)_2Cl]^+$, $[Os(phen)_2Cl]^+$, $[Ru(bpy)_2]^{2+}$, $[Rh(bpy)_2]^{2+}$, cobalt phthalocyanine, ferrocenes, methylene blue, methylene green, 7,7,8,8-tetracyanoquinodimethane, tetrathiafulvalene, toluidine blue, meldola blue, N-methylphenazine methosulfate, phenyldiamines, 3,3',5,5'-tetramethylbenzidine, pyrogallol, and benzoquinone wherein phen is 1,10-phenanthroline and bpy is 2,2'-bipyridine.

8. The method of claim 1 further comprising fabricating said reagent matrix by selecting said oxidase from oxidases capable of producing hydrogen peroxide.

9. The method of claim 8 further comprising fabricating said reagent matrix by selecting said oxidase from the group consisting of glucose oxidase, acyl-CoA oxidase, N-acylhexosamine oxidase, D-amino acid oxidase, cholesterol oxidase, fructosyl-peptide oxidase, glutamate oxidase, L-α-glycerophosphate oxidase, lactate oxidase, putrescine oxidase, pyranose oxidase, pyruvate oxidase, sarcosine oxidase, uricase, and xanthine oxidase.

10. The method of claim 1 further comprising fabricating said reagent matrix by selecting said peroxidase from the group consisting of soybean peroxidase and horseradish root peroxidase.

11. The method of claim 1 further comprising fabricating said reagent matrix by including one or more of the materials selected from the group consisting of a surfactant, a polymer binder, an inactive bulking agent, and an antioxidant.

12. The method of claim 11 further includes selecting said surfactant from the group consisting of anionic, cationic, non-ionic, and zwitterionic detergents.

13. The method of claim 11 further includes selecting said surfactant from the group consisting of Triton X-100, Tween 20, sodium cholate hydrate, hexadecylpyridinium cholide monohydrate, and CHAPs.

14. The method of claim 11 further includes selecting said polymer binder from the group consisting of polyvinylpyrrolidone, polyethylene oxide, poly(vinyl alcohol), poly(ethylene glycol), poly(propylene glycol), polysulfone, carboxy methyl cellulose, hydroxypropyl cellulose, methyl cellulose, and poly(2-ethyl-2oxazoline).

15. The method of claim 11 further includes selecting said polymer binder to be a mixture of polyethylene oxide and methyl cellulose.

16. The method of claim 11 further includes selecting said inactive bulking agent from the group consisting of trehalose, galactose, suctose, lactose, mannitol, mannose, fructose, sucrose, lactose, lactitol, sorbitol, xylitol, and maltose.

17. The method of claim 11 further includes selecting said antioxidant from the group consisting of reductants and oxygen scavengers.

18. The method of claim 11 further includes selecting said antioxidant from the group consisting of sodium sulfite, sodium hydrosulfite, hydrazine, hydroquinone, carbohydrazide, N,N-Diethylhydroxylamine, methylethylketoxime, diethylthreitol, erythorbic acid, and ascorbic acid.

* * * * *

UNITED STATES PATENT AND TRADEMARK OFFICE
CERTIFICATE OF CORRECTION

| | | |
|---|---|---|
| PATENT NO. | : 7,648,624 B2 | Page 1 of 1 |
| APPLICATION NO. | : 11/161180 | |
| DATED | : January 19, 2010 | |
| INVENTOR(S) | : Cai et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1065 days.

Signed and Sealed this

Twenty-third Day of November, 2010

David J. Kappos
*Director of the United States Patent and Trademark Office*